United States Patent [19]

Yamashita et al.

[11] Patent Number: 4,824,205

[45] Date of Patent: Apr. 25, 1989

[54] APPARATUS FOR IMPROVING IMAGE FORMED BY IMAGING OPTICAL SYSTEM

[75] Inventors: Nobuo Yamashita; Susumu Takahashi, both of Hachiouji; Hiroshi Matsui, Hino, all of Japan

[73] Assignee: Olympus Optical Co., Ltd., Tokyo, Japan

[21] Appl. No.: 94,739

[22] Filed: Sep. 9, 1987

[30] Foreign Application Priority Data

Sep. 9, 1986 [JP] Japan .................................. 61-210527
Sep. 22, 1986 [JP] Japan .................................. 61-224537

[51] Int. Cl.$^4$ .............................................. G02B 6/06
[52] U.S. Cl. .............................. 350/96.25; 350/96.26; 350/286; 350/287
[58] Field of Search ............... 350/6.2, 6.3, 6.4, 96.24, 350/96.25, 96.26, 286, 287

[56] References Cited

U.S. PATENT DOCUMENTS

| | | | |
|---|---|---|---|
| 3,016,785 | 1/1962 | Kapany | 350/96.25 |
| 3,110,762 | 11/1963 | Frank | 350/96.25 X |
| 3,217,588 | 11/1965 | Chitayat | 350/96.25 |
| 3,217,589 | 11/1965 | Chitayat | 350/96.25 |
| 3,554,632 | 1/1971 | Chitayat | 350/96.25 |
| 3,740,115 | 6/1973 | Cole | 350/96.26 |
| 4,141,624 | 2/1979 | Siegmund | 350/96.26 |
| 4,154,502 | 5/1979 | Siegmund | 350/96.26 |
| 4,253,447 | 3/1981 | Moore et al. | 350/96.26 X |
| 4,378,952 | 4/1983 | Siegmund | 350/96.25 |
| 4,618,884 | 10/1986 | Nagasaki | 350/96.26 X |

FOREIGN PATENT DOCUMENTS 56-40546 9/1981 Japan .
57-46211 3/1982 Japan .

Primary Examiner—John D. Lee
Attorney, Agent, or Firm—Cushman, Darby & Cushman

[57] ABSTRACT

An image forming optical system designed in simple composition and capable of providing images of high quality, said optical system comprising a prism system including at least a pair of a first prism arranged on the optical axis between an objective lens and an incident end face of an image guide or solid-state image sensor and having an emerging face inclined relative to the optical axis and a second prism having an incident surface inclined relative to the optical axis, and so adapted as to vibrate at least one of said first and second prisms in the direction of the optical axis by a piezoelectric element type of actuator. Said image forming optical system is so composed as to be suited for use with fiber scopes, electronic fiber scopes or display scopes.

25 Claims, 8 Drawing Sheets

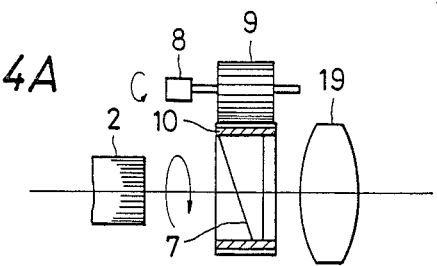
FIG. 4A
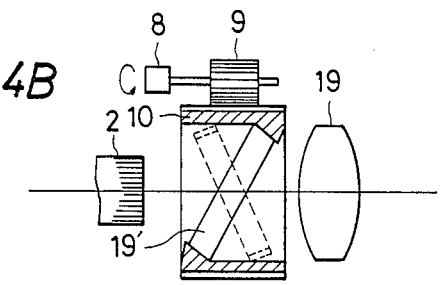
FIG. 4B
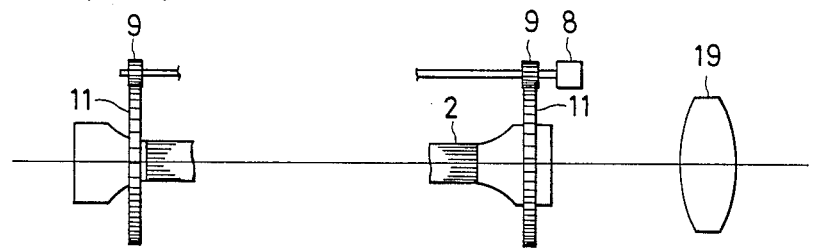
FIG. 4C
FIG. 4D
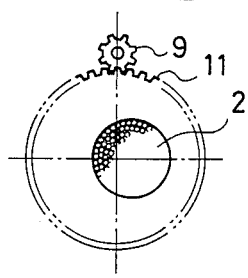
FIG. 5
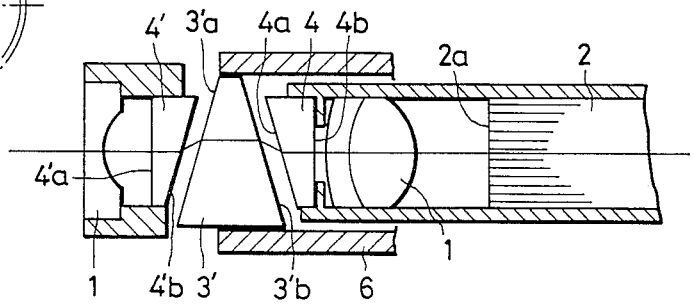

APPARATUS FOR IMPROVING IMAGE FORMED BY IMAGING OPTICAL SYSTEM

BACKGROUND OF THE INVENTION (a) Field of the Invention

The present invention relates to an improvement of an image forming optical system and more particularly to an image forming optical system which is suited for use in endoscopes or fiber scopes and the like.

(b) Description of the Prior Art

In the field of optical instruments such as fiber scopes which receive images of objects on an end surface of an image guide composed by bundling a large number of fibers and transmit said images to the other end surface of the image guide, it is already known that quality of the images observed on the emerging end surface of the image guide is improved by vibrating relative position between the incident end surface of the image guide and the object images at a high frequency (to a degree permitting to utilize the after image effect of the eye) and at a very narrow amplitude (on the order of the thickness of the fiber) (for example, refer to S. Kapany "Fibers Optics" ACADEMIC PRESS 1967).

By utilizing this phenomenon, attempts have conventionally been made to improve qualities of images observed through fiber scopes. For example, Japanese Preliminary Patent Publication Sho No. 57-46211 discloses a fiber scope in which a permanent magnet is fixed to an outer circumference of a lens element of an objective lens system arranged before the incident end surface of an image guide and connected by way of a cushion to an AC solenoid fixedly attached to the image guide. Said fiber scope improves image quality by adopting such a composition as to vibrate an image of object on the incident end surface of the image guide by vibrating said lens element under the action of an alternating magnetic field produced by applying AC current to an AC solenoid. On the other hand, the same composition is adopted also on the emerging side of the image guide to vibrate the image emerging from the image guide in synchronization with the vibration on the incident side, thereby preventing the observed images from being blurred due to the vibration of said lens element.

In the conventional example described above wherein said lens element is vibrated on both the sides of an axis perpendicular to the optical axis, however, a surplus space must preliminarily be reserved around said lens element in its diametrical direction since the edge line on the outer circumference of said lens element protrudes in the direction of the outside diameter thereof. Accordingly, it posed a problem that the distal end of the fiber scope was inevitably thickened.

Further, there are widely used so-called electronic fiber scopes which use solid-state image sensors in place of said image guide. For such electronic fiber scopes which require very small image sensors, it is a very important problem how to enhance resolution. Japanese Patent Publication Sho No. 56-40546 discloses a method to solve the problem. This method improves resolution by arranging plural number of image sensors at positions deviating from the optical axis for a distance corresponding to ½ or ⅓ of the pitch reserved between two neighboring picture elements on the plane perpendicular to the optical axis of the imaging lens so that the relative positions are different from each other between one row of the picture elements and the other row of the picture elements and obtaining the information corresponding to the areas between the picture elements of one image sensor from the other image sensor.

In the fiber scopes, however, it is difficult from viewpoint of space, in the first place, to arrange plural number of solid-state image sensors, beam splitters for leading lights thereto, etc. in the distal ends. In addition, the fiber scope of the type described above requires preliminarily arranging plural number of solid-state image sensors at positions deviating from each other for the purpose of adjusting deviating distance of images to a predetermined value, thereby requiring high positioning precision for said sensors and making it tedious to assemble the image sensing system.

SUMMARY OF THE INVENTION

A primary object of the present invention is to provide an image forming optical system permitting to obtain images of higher quality without increasing its accommodating space.

Another object of the present invention is to provide an image forming optical system suited for use in fiber scopes.

According to the present invention, these objects are accomplished by arranging a prism system including at least a first prism having an emerging surface inclined relative to the optical axis and a second prism having an incident surface inclined relative to the optical axis at a position on the optical axis between the objective lens or imaging lens and an image receiving means for receiving an image formed by said objective lens or imaging lens, whereby at least either of said first and second prisms is vibrated in the direction of the optical axis and accordingly the image is vibrated on the image receiving surface of said image receiving means in the direction perpendicular to the optical axis.

In a preferred formation of the present invention, the image receiving means is designed as the incident end face of an optical fiber bundle or solid-state image sensor, the emerging surface of said second prism is inclined in such a manner that the normal thereof is located on a plane which is the same or mutually different from that of the incident surface of said second plane and said first or second prism is vibrated with a piezoelectric element type of actuator. Therefore, this formation facilitates assembly of the optical system and enables assembly of said optical system into a fiber scope.

These and other objects as well as the features and advantages of the present invention will be apparent from the following detailed description of the preferred embodiments when taken in conjunction with the accompanying drawings.

BRIEF DESCRIPTION OF THE DRAWINGS

FIGS. 4A, 4B, 4C and 4D show sectional views illustrating various types of compositions of the eyepiece for said applicational example;

FIG. 5 shows a sectional view illustrating a second embodiment of the image forming optical system according to the present invention;

DESCRIPTION OF THE PREFERRED EMBODIMENTS

Figure 1:
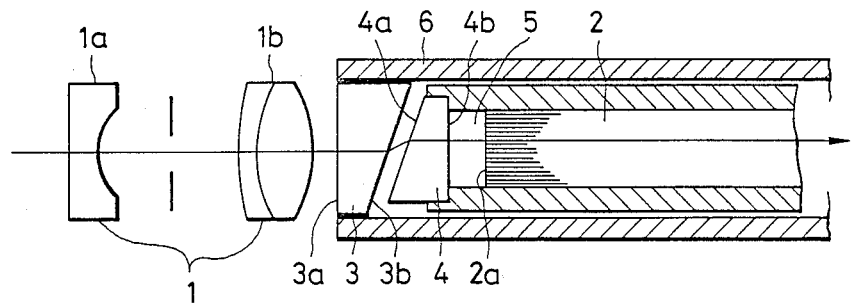
FIG. 1 shows in section a first embodiment of the image forming optical system according to the present invention.

Now, the Embodiment 1 of the optical system according to the present invention will be described with reference to FIG. 1 and FIG. 2. This embodiment adopts a composition suited for use in a fiber scope and uses as an image receiving means the incident end surface of the image guide composed of a optical fiber bundle. That is to say, a prism optical system consisting of a vibrating prism 3 and a fixed prism 4 is arranged between an objective lens 1 including a concave lens element 1a also serving as a cover glass and a convex lens element 1b and an incident end surface 2a of an image guide 2. Incident surface 3a of the vibrating prism 3 is perpendicular to the optical axis, whereas emerging surface 3b thereof is inclined relative to the optical axis. Emerging surface 4b of the fixed prism 4 is perpendicular to the optical axis and cemented to incident end face 2a of the image guide 2 with a cover glass 5 interposed, whereas incident surface 4a of the fixed prism 4 is inclined relative to the optical axis and parallel to the emerging surface 3b of the vibrating prism 3. Fixedly attached to the outer circumference of the vibrating prism 3 is one end of an actuator composed of rod-shaped piezoelectric elements. The other end of the actuator 6 is fixed to a suitable location on the main body of a fiber scope (not shown).

Accordingly, when an AC voltage is applied to the actuator composed of piezoelectric elements from a power source E, the actuator elongates and contracts in the direction of the optical axis, thereby vibrating the vibrating prism 3 back and forth along the optical axis.

Figure 2:
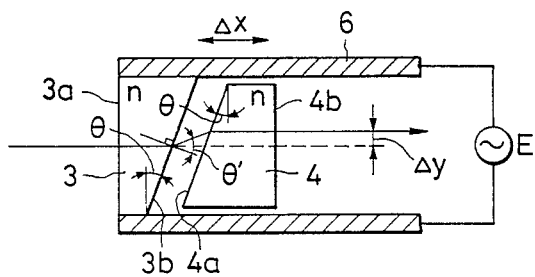
FIG. 2 shows a schematic representation illustrating functional principle of said first embodiment.

FIG. 2 shows a sectional view descriptive of functional principle of the Embodiment 1. As is apparent from this drawing, light is refracted upward by the emerging surface of the vibrating prism 3 upon emerging therefrom, refracted again by the incident surface 4a of the fixed prism 4 upon being incident thereon and emerges from the fixed prism 4 in the direction parallel to the original light. Because of these refractive functions, difference between height of the incident light and that of emerging light of the prism system is varied when the interval between both the prisms 3 and 4 is changed. Let us now designate vibration amplitude of the actuator 6 by $\Delta x$, refractive index of both the prisms by n, inclination angle of the emerging surface 3b of the vibrating prism 3 (or inclination angle of the incident surface 4a of the fixed prism 4) by $\theta$ and emerging angle of the vibrating prism 3 by $\theta'$ respectively. Then, amplitude $\Delta y$ of the optical axis of the light emerging from the prism system (or amplitude of the image on the incident end face 2a of the image guide 2) is given as follows:

$$\Delta y = \Delta x \frac{\cos \theta}{\cos \theta'} \sin (\theta' - \theta)$$

$$\sin \theta', = n \sin \theta$$

Therefore, it is sufficient to determine size of the piezoelectric element type of actuator 6, refractive indices of the prisms 3 and 4, and inclination angle of the surfaces respectively so as to obtain a desired value of $\Delta y$.

Figure 3:
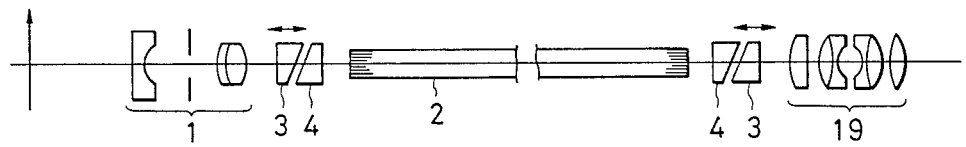
FIG. 3 shows a schematic sectional view illustrating an applicational example of said first embodiment.

In addition, it is desirable to cancel vibration of the image on the incident end face 2a of the image guide 2 since such vibration causes vibration of the image observed on the side of the eyepiece, thereby hindering proper observation. Like the conventional example wherein vibration on the incident side is cancelled by vibrating the image on the emerging side in synchronization with and at the same amplitude as that on the incident side with a vibrating mechanism having the same composition as that on the incident end face provided also on the emerging end face of the image guide 2, the present invention allows to arrange the above-described vibrating mechanism, as shown in FIG. 3, between the emerging end face of the image guide 2 and the eyepiece lens 19. Further, since it is generally unnecessary to design the emerging side of the image guide 2 so compact, it is possible to adopt the composition according to the prior art for this side or vibrate the emerging end face of the image guide 2 directly in the direction perpendicular to the optical axis. That is to say, it is possible to adopt the various compositions illustrated in FIGS. 4A through 4C. FIG. 4A illustrates a composition wherein the prism 7 arranged between the eyepiece lens 19 and the image guide 2 is rotated at a predetermined speed by a motor 8, gear 9 and supporting frame gear 10, whereas FIG. 4B shows another composition wherein a glass plate 19' having parallel surfaces and arranged obliquely relative to the optical axis between the eyepiece lens 19 and the image guide 2 is rotated at a predetermined speed by the motor 8, gear 9 and supporting gear 10. Shown in FIG. 4C is a third composition wherein the end of the image guide 2 is eccentrically rotated or vibrated by the motor 8, gear 9 and eccentric gear 11. (See FIG. 4D)

FIG. 5 illustrates the Embodiment 2 of the present invention wherein a structure consisting of a vibrating prism 3' sandwiched between two fixed prisms 4' and 4 is assembled in the objective lens 1. The incident surface 4′a of the fixed prism 4′ is perpendicular to the optical axis and emerging surface 4′b thereof is inclined relative to the optical axis, whereas the incident surface 4a of the fixed prism 4 is inclined relative to the optical axis in the direction opposite to the emerging surface 4′b and the emerging surface 4b thereof is perpendicular to the optical axis. The incident surface 3′a of the vibrating prism 3′ is inclined in the direction parallel to the emerging surface 4′b of the fixed prism 4′ and the emerging surface 3′b thereof is inclined in the direction parallel to the incident surface 4a of the fixed prism 4.

Figure 6:
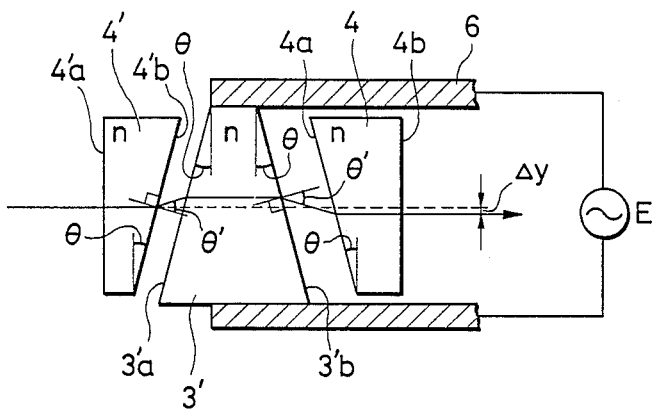
FIG. 6 shows a sectional view illustrating functional principle of said second embodiment.

Shown in FIG. 6 is a schematic view descriptive of functional principle of the Embodiment 2. As is seen from this drawing, light is refracted upward upon emerging from the fixed prism 4′, refracted again by the incident surface 3′a of the vibrating prism 3′ upon being incident thereon in the direction parallel to the original light, refracted downward upon emerging from the vibrating prism 3′ and refracted by the incident surface 4a of the fixed prism 4 upon being incident thereon in the direction parallel to the original light, thereafter emerging from the fixed prism 4. In this case, relationship between vibration amplitude $\Delta x$ of the piezoelectronic element type of actuator 6 and amplitude $\Delta y$ of the optical axis emerging from the prism system is:

$$\Delta y = 2 \Delta x \frac{\cos \theta}{\cos \theta'} \sin (\theta' - \theta)$$

$$\sin \theta' = n \sin \theta$$

wherein the reference symbols n, $\theta$ and $\theta'$ represent the same factors as those defined in the Embodiment 1.

In the Embodiment 2 wherein amplitude $\Delta y$ is amplified to a degree equal to magnification $\beta$ of the optical system arranged after the fixed prism 4, amplitude of the image on the incident end face 2a of the image guide 2 is expressed as $\Delta y$. Therefore, the Embodiment 2 gives image displacement $2\beta$ times as long as that obtained by the Embodiment 1 and enables to minimize amplitude of the piezoelectric element type of actuator 6 to $\Delta x/2\beta$ on an assumption of an equal image amplitude, thereby making it possible to use a shorter piezoelectric element type of actuator and realize a fiber scope having shorter distal end.

Figure 7A:
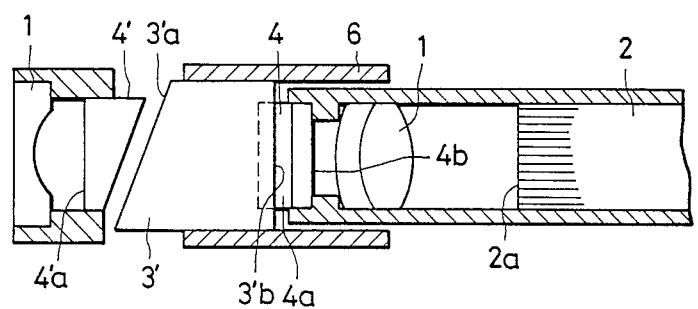
FIGS. 7A and 7B show a sectional view illustrating composition and a perspective view of the main parts illustrating functional principle of a third embodiment of the image forming optical system according to the present invention.
Figure 7B:
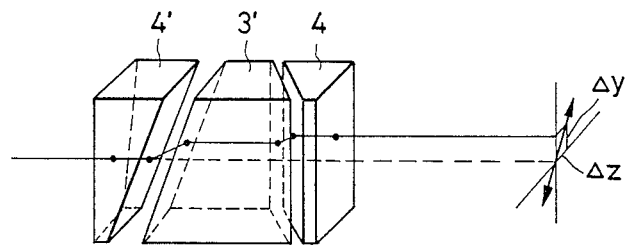

FIGS. 7A and 7B illustrate composition and functional principle of the Embodiment 3 of the present invention incorporating the vibrating prism 3′ sandwiched between the two fixed prisms 4′ and 4 wherein the emerging surface 4′b of the first fixed prism 4′, incident surface 3′a of the vibrating prism 3′, emerging surface 3′b of the vibrating prism 3′ and incident surface 4a of the second fixed prism 4 are parallel to one another, whereas the normal of the incident surface 3′a of the vibrating prism 3′ is located on the plane of the paper and the normal of the emerging surface 3′b of the vibrating prism 3′ is located on the plane perpendicular to the paper.

In this case, the image vibration has amplitude $\Delta y$ on the paper plane and amplitude $\Delta z$ in the direction perpendicular to the paper plane. However, since $\Delta y$ and $\Delta z$ have the same phase, the image is vibrated along a plane having a certain inclination angle.

Figure 8:
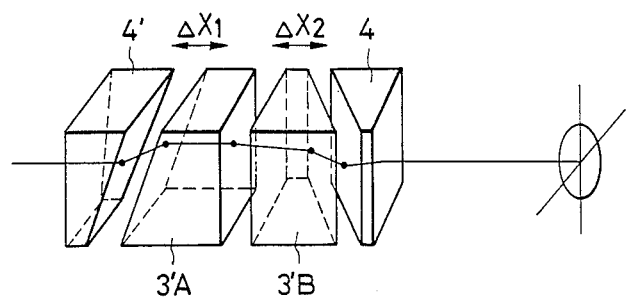
FIG. 8 shows a perspective view illustrating the main parts of a variant of said third embodiment.

FIG. 8 shows main parts for a variant example of the Embodiment 3. In this example, the vibrating prism 3′ is cut along a plane perpendicular to the light into two vibrating prisms 3′A and 3′B. The image is moved up and down when the first vibrating prism 3′A is moved back and forth along the optical axis, whereas the image is displaced in the direction perpendicular to the paper surface when the second vibrating prism 3′B is displaced back and forth along the optical path. When angular frequency of the vibration of the first vibrating prism 3′A is designated by $\omega_1$ and angular frequency of the vibration of the second vibrating prism 3′B is represented by $\omega_2$, the displacement distances are proportional to $\Delta x_1 \sin(\omega_1 t + \phi_1)$ and $\Delta x_2 \sin(\omega_2 t + \phi_2)$ respectively. Therefore, the displacement locus of the light emerging from the prism system can be various shapes such as a straight line, circle and ellipse by properly determining the respective angular frequencies of the vibration $\omega_1$ and $\omega_2$, initial phase (relative positional relationship between the two vibrating prisms 3′A and 3′B), $\phi_1$ and $\phi_2$.

Figure 9:
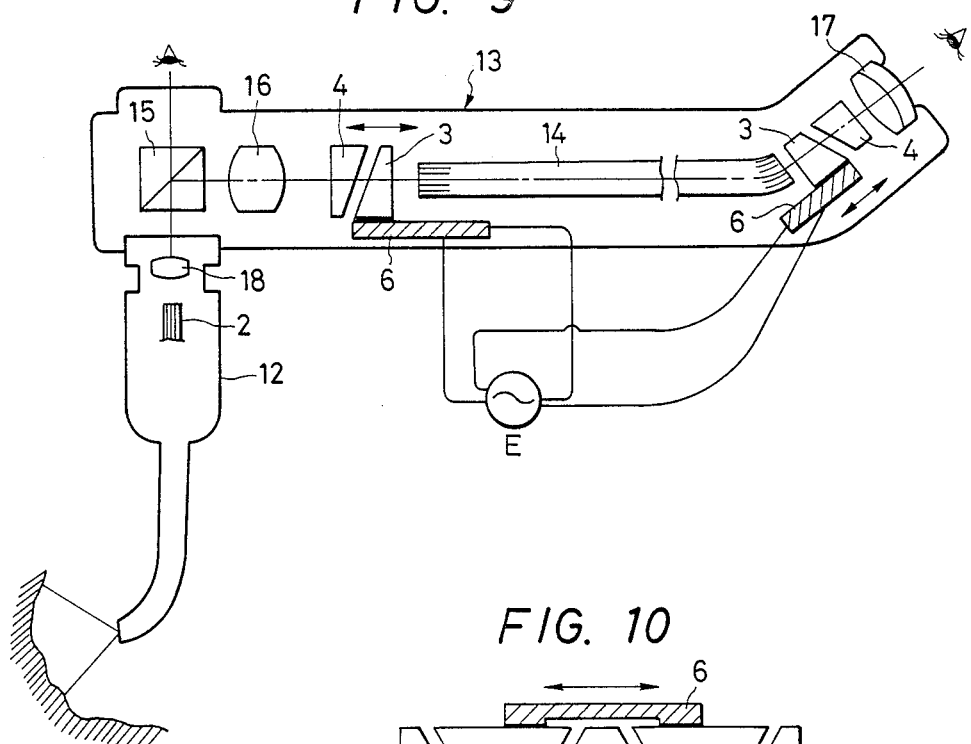
FIG. 9 shows a schematic sectional view illustrating a fourth embodiment of the image forming optical system according to the present invention.

FIG. 9 illustrates the Embodiment 4 of the present invention wherein the above-described vibrating mechanism is arranged before and after an image guide 14 of a display scope attached to the eyepiece of a fiber scope for allowing plural persons to observe an image at the same time. The display scope is equipped with a beam splitter 15, and an imaging lens 16, fixed prism 4, vibrating prism 3, image guide 14, vibrating prism 3, fixed prism 4 and eyepiece lens 17 are arranged consecutively along the optical path. Since the emerging end surface of the image guide 2 arranged in the fiber scope 12 is focused on the incident end surface of the image guide 14 by the eyepiece lens 18 and imaging lens 16, it is possible to improve image quality by arranging said image vibrating mechanism in the optical path between the beam splitter 15 and the incident end face of the image guide 14, and vibrating the image on the incident end face of the image guide 14. Further, since the mesh structure on the end face of the image guide is made invisible by vibrating the image, the vibration is effective also for eliminating the moiré produced due to interference between the mesh structures on the emerging end face of the image guide 2 in the fiber scope and the incident end face of the image guide 14 in the display scope 13 respectively.

Figure 10:
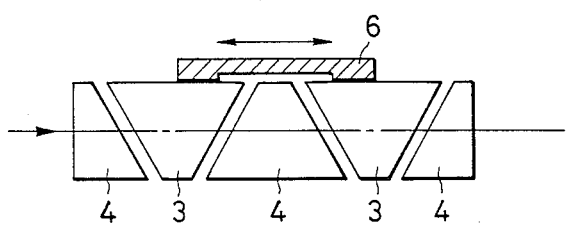
FIG. 10 shows a schematic sectional view illustrating the main parts of a fifth embodiment of the image forming optical system according to the present invention.

FIG. 10 shows the Embodiment 5 of the present invention wherein two vibrating prisms 3 are arranged between three fixed prisms 4 so as to permit displacing both the vibrating prisms 3 in synchronization and in the same direction. This embodiment has advantages to allow images to be displaced for a distance twice as long and minimize amplitude of the piezoelectric element type of actuator 6.

Figure 11:
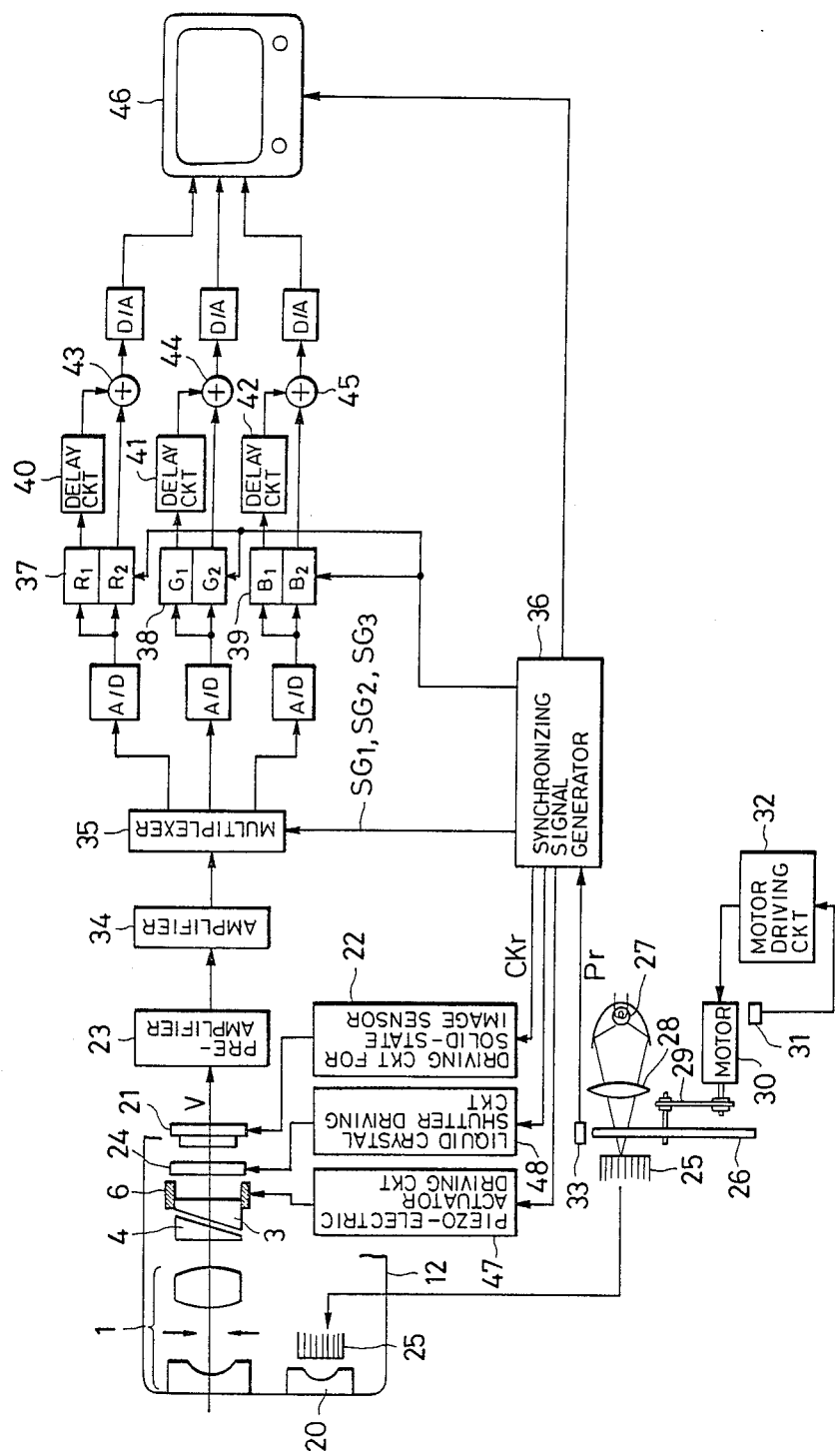
FIG. 11 shows a diagram illustrating an example of electronic fiber scope incorporating a sixth embodiment of the image forming optical system according to the present invention.
Figure 12:
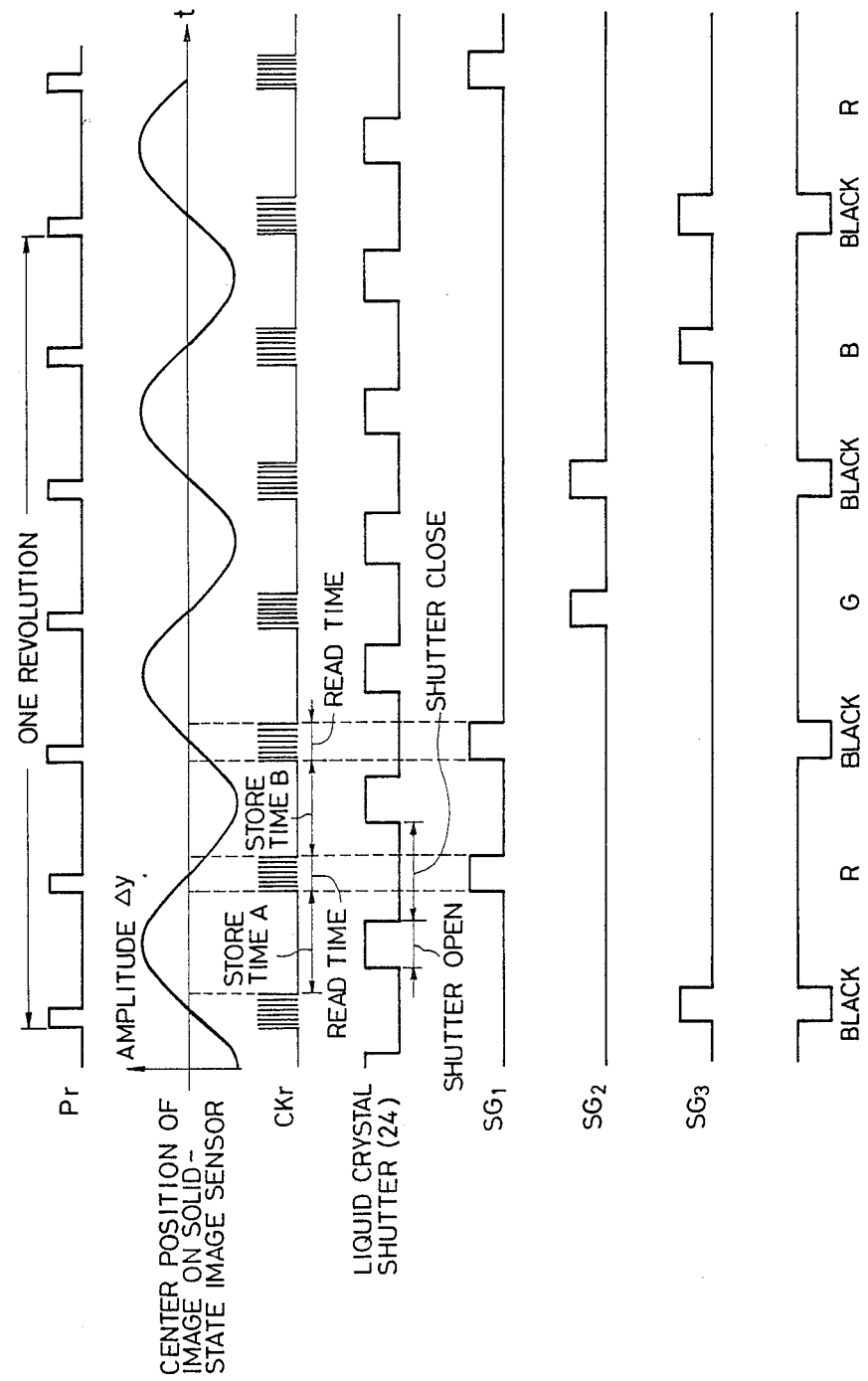
FIG. 12 shows a timing chart describing actions of the electronic fiber scope illustrated in FIG. 11.
Figure 13:
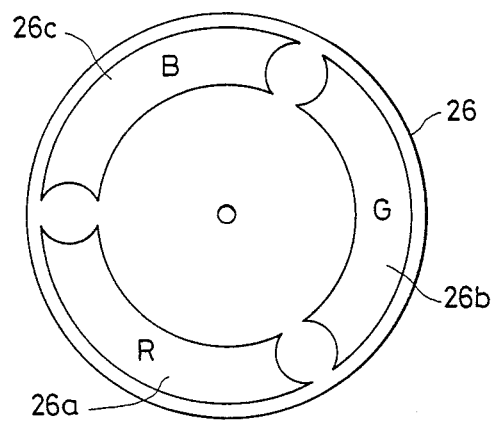
FIG. 13 shows a front view of the rotating filter used in the electronic fiber scope illustrated in FIG. 11.

FIG. 11 shows the Embodiment 6 of the present invention using solid-state image sensors in place of the image guide as an image receiving means. Referring to FIG. 11 through FIG. 14, this embodiment will be detailedly described below on an assumption that it is assembled in an electronic fiber scope of a type irradiating with rays R, G and B consecutively and using the same reference symbols for the elements or parts which are substantially the same as those employed in the preceding embodiments. In the composition shown in FIG. 11, an illumination lens 20 is arranged parallely to the objective lens 1 in the distal end of the fiber scope 12, a solid-state image sensor 21 of the line transfer type is provided after the objective lens 1, a received optical image is converted into video signals V by a solid-state image sensor driving circuit 22 and the video signals V are transferred through an amplifier 23 to the circuit at the next stage. Further, the vibrating prism system, i.e., vibrating prism 3, fixed prism 4 and liquid crystal shutter 24, is arranged between the objective lens 1 and the solid-state image sensor 21 so that an image of object is vibrated on the light receiving surface of the solid-state image sensor 21 in the direction perpendicular to the optical axis. Arranged after the illumination lens 20 is a light guide composed of optical fibers or the like and the rear end face thereof is so adapted as to be irradiated with illumination light through a rotating filter 26. The illumination light is emitted from a light source lamp 27 and irradiates the rotating filter 26 through a lens 28. The illumination light is allowed to be incident on the incident end face of said light guide 25 at suitable light-shielding intervals through R (red) filter 26a, G (green) filter 26b and B (blue) filter alternately arranged. The rotating shaft of the rotating filter 26 is connected to a motor 30 through a transmission system 29 and rotating speed of the motor 30 is maintained constant by controlling a motor driving circuit 32 with signals provided from a rotation detecting element 31 arranged on the motor 30. Further, a rotation detecting element 33 is arranged on the outer circumference of the rotating filter 26 for signal readout from the solid-state image sensor 21 and synchronization with the rotation of the rotating filter 26. On the other hand, the video signals V are amplified by an amplifier 34 and then input into a multiplexer 35. The multiplexer consists of three switches corresponding to input signals R, G and B. These switches are changed over consecutively at a predetermined frequency by gate signals $SG_1$, $SG_2$ and $SG_3$ for these switches provided from a synchronizing signal generator 36, and supply video signals corresponding to frame memories 37, 38 and 39 for R, G and B respectively through an A/D converter. The color signals stored in the frame memories 37, 38 and 39 are read out by the function of the synchronizing signal generator 36, fed through delay circuits 40, 41 and 42, and composed through mixers 43, 44, 45 and D/A converters for display on a color TV monitor 46. In the embodiment described above, the rotation detecting element 33 functions to detect intermediate positions and end positions of the R, G and B filters arranged in the rotating filter 26 in the rotating direction thereof, and feed its detection pulses Pr to the synchronizing signal generator 36. The synchronizing signal generator controls the driving circuit 47 for the piezoelectric element type of actuator 6 by using the detection pulses Pr, and the piezoelectric element type of actuator 6 vibrates the prism 3 of the vibrating prism system, thereby vibrating the image of object on the sensitive surface of the solid-state image sensor in the direction perpendicular to the optical axis. Further, the synchronizing signal generator creates readout clock signals CKr by using the detection pulses Pr (FIG. 12), and converts electric charges stored in the solid-state image sensor 21 into video signals V for R, G and B by controlling said driving circuit 22. In this case, since it is sufficient to obtain video signals representing the image of object only at the peak and valley of the vibration, the function of the vibrating prism 3 is synchronized with that of the solid-state image sensor 21 so that the peak area and valley area of the vibration are located within the storage time of the solid-state image sensor, and the time for signal readout from the solid-state image sensor is located between both the areas. That is to say, timings of the rotation of the rotating filter 26, vibration of the image, image sensing and readout are designed in such a manner that the storage time is set twice while one color filter of the rotating filter 26 is positioned between the light guide 25 and lens 28, the first readout time is synchronized with the intermediate position of said filter and the second readout time is synchronized with the light shield between said filter and another filter. Moreover, the synchronizing signal generator 36 drives the liquid crystal shutter 24 by controlling the liquid crystal shutter driving circuit 48 with the detection pulses Pr. The liquid crystal shutter 24 is adopted as an auxiliary means performing the functions described below. When the storage time is long as shown in FIG. 12, the image shifts on the sensitive surface of the solid-state image sensor during the storage time and the video signals obtained from the solid-state image sensor include components corresponding to a state other than the stationary state of the image at the peak or valley of the vibration, thereby producing deformation of a certain degree after image reproduction with no correction. In order to prevent this phenomenon, the solid-state image sensor must be irradiated with light only while the image is located very close to the peak or valley of the vibration. This purpose can be achieved and the video signals can be purified by operating the liquid crystal shutter 24 as a transparent or shielding means at the timing illustrated in FIG. 12. Furthermore, the synchronizing signal generator 36 is so composed as to input the R, G and B video signals to the frame memories 37, 38 and 39 respectively while switching the multiplexer 35 by creating gate signals $SG_1$, $SG_2$ and $SG_3$ for the above-mentioned switches respectively with the detection pulses Pr (FIG. 12). Each of the frame memories 37, 38 and 39 corresponding to R, G and B signals respectively consists of two parts $R_1$, $R_2$, $G_1$, $G_2$ or $B_1$, $B_2$. Connected to one part $R_1$, $G_1$ or $B_1$ is the delay circuit 40, 41 or 42. Delay time provided by each delay circuit 40, 41 or 42 corresponds to ½ pitch of the picture element. In this case, $\Delta y$ is selected in such a manner that it is equal to ¼ of the pitch between the picture elements of the solid-state image sensor.

Figure 14:
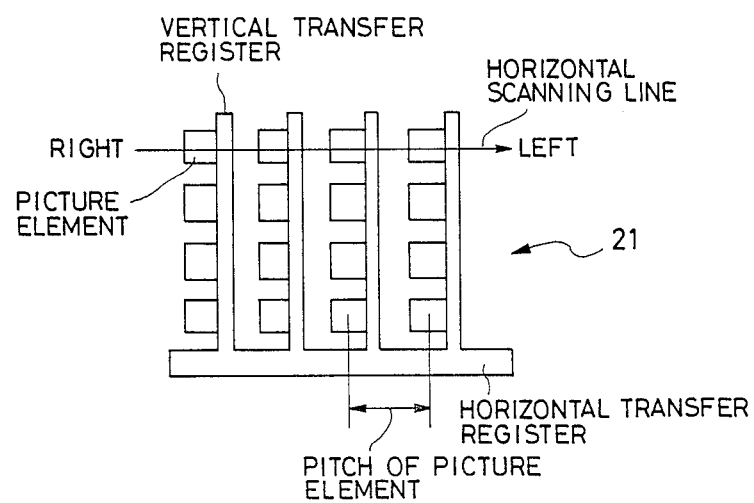
FIG. 14 shows an enlarged view of the solid-state image sensor used in the electronic fiber scope illustrated in FIG. 11.

Since the electronic fiber scope incorporating the Embodiment 6 is composed as described above, signals are read out twice from the solid-state image sensor while an object is irradiated with R, G or B light. The video signals obtained during the storage time A, for example, shown in FIG. 12 are stored into $R_1$ of the memory 37, and the video signals obtained during storage time B are stored into $R_2$ of the memory 37. The video signals of the other colors G and B are stored in the similar way. In this case, since amplitude of the image is set at ¼ pitch of the picture element and the video signals are stored into the solid-state image sensor only while the image is located very close to the peak or valley of the vibration, the video signals stored into $R_1$ and $R_2$ of the frame memory 20 are deviated from each other by ½ pitch of the picture element, or the signals mutually compensate the areas between the picture elements of the other type of signals. When the solid-state image sensor 21 is of the line transfer type as shown in FIG. 14, for example, and video signals including components representing a peak shifted rightward obtained during horizontal scanning of an image are stored into $R_1$ of the frame memory 20 whereas video signals including components representing a peak shifted leftward are stored into $R_2$ of the frame memory 20, the signals of $R_1$ and $R_2$ can be compensated correctly by delaying the signals of $R_1$ by ½ pitch of the picture element for composition with signals of $R_2$. The delay circuit 40 and mixer 43 are provided for this purpose. However, the same effect can be obtained simply by making the timing for signal readout from $R_1$ later by ½ pitch of the picture elements than that from $R_2$. This applies also to video signals of the other colors G and B. Since the Embodiment 6 permits obtaining both the types of video signals corresponding to the area between the picture elements by the vibration of image as described above, it is capable of providing images of high resolution. Further, the Embodiment 6 allows to adjust vibration amplitude after assembly of the optical instrument, and facilitate assembly of the optical system.

Figure 15:
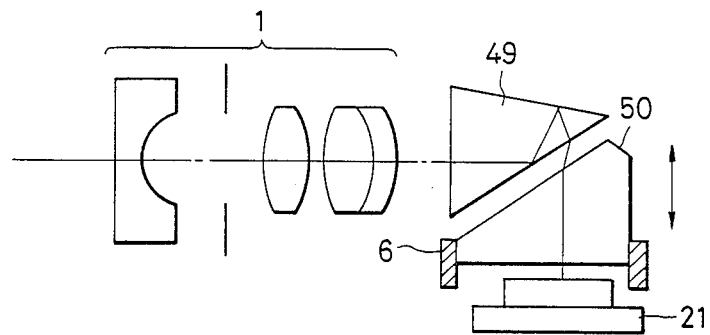
FIG. 15 shows a sectional view illustrating a seventh embodiment of the image forming optical system according to the present invention.

FIG. 15 illustrates an image forming optical system as the Embodiment 7 wherein the solid-state image sensor is arranged in the longitudinal direction of a fiber scope, and an optical path change-over prism system consisting of a fixed prism 49 and vibrating prism 50 is arranged between the objective lens 1 and the solid-state image sensor 21. This embodiment is so adapted as to vibrate an object image on the sensitive surface of the solid-state image sensor by vibrating the vibrating prism 50 along the optical path indicated by an arrow (perpendicular to the optical axis of the objective lens 1).

Though the Embodiment 6 is so designed as to vibrate an image in the horizontal direction, it is possible to vibrate an image in the vertical direction. In the latter case, a solid-state image sensor of the field storage type and having a small number of lines, for example, can provide resolution as high as that obtained with the frame-storage type of solid-state image sensor with no necessity of special operations in the circuits. The vibration system of the Embodiment 6 can be used for further enhancing resolution with the frame-storage type of solid-state image sensor. Further, it is possible to improve resolution in both the vertical and horizontal directions by selecting an oblique vibrating direction. For this purpose, it is sufficient to return the second field for the time corresponding to the distance of the horizontal component of vibration until it is located between the scanning lines of the first field. Different scanning modes will also be compatible with the Embodiment 6.

Moreover, it will be needless to say that the image sensing systems illustrated in FIG. 11 and FIG. 15 are applicable not only to fiber scopes but also widely to image forming optical systems for instruments such as TV cameras which are employed for obtaining object images with solid-state image sensors.

Figure 16:
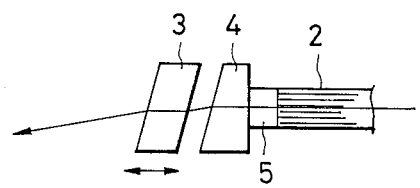
FIG. 16 shows a sectional view illustrating the main parts of an eighth embodiment of the image forming optical system according to the present invention.
Figure 17:
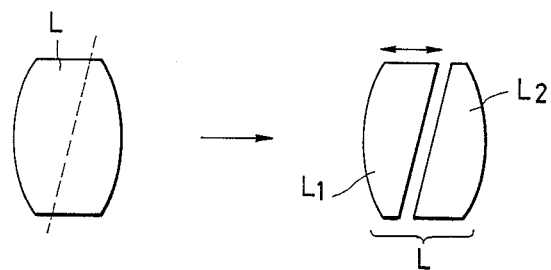
FIG. 17 shows a sectional view illustrating the main parts of a ninth embodiment of the image forming optical system according to the present invention.

In addition, the oblique surfaces opposite to each other of the prisms are not necessarily parallel to each other though they are parallel in the embodiments described above. If the parallelism is degraded remarkably, however, the airspace will aggravate astigmatism. Oblique angles of the prisms should therefore be properly determined taking astigmatism into consideration. Further, the image forming optical system will be of an oblique view type as shown in FIG. 16 if the incident surface 3a of the vibrating prism 3 is not perpendicular to the optical axis in the Embodiment 1. Therefore, angle of this surface may be inclined to various degrees for proper application. Furthermore, it is needless to say that the lens element L can be split into a movable lens part $L_1$ and a fixed lens part $L_2$ as shown in FIG. 17 for operating it as a prism.

What is claimed is:
1. An apparatus for improving an image formed by an imaging optical system comprising:
   an objective lens;
   an image receiving means for receiving an image formed by said objective lens;
   a prism system means arranged on an optical axis between said objective lens and said image receiving means, said prism system means including:
      a first prism means having an incident surface and an emerging surface which is arranged to be inclined surface to said optical axis, and
      a second prism means having an incident surface which is spaced from the emerging surface of said first prism means and an emerging surface; and
   a driving means for vibrating at least one of said first and second prism means along said optical axis in such a manner that angles made by the incident and emerging surfaces of said first and second prism means with said optical axis are not varied and said image formed by said objective lens is vibrated in a direction perpendicular to said optical axis due to the vibration of at least one of said first and second prism means.

2. An apparatus according to claim 1 wherein the emerging surface of said second prism means is inclined relative to the optical axis in such a manner that the normal thereof is located on the same plane as the normal of the incident surface of said second prism means.

3. An apparatus according to claim 2 wherein the emerging surface of said first prism means is parallel to the incident surface of said second prism means.

4. An apparatus according to claim 3 wherein amplitude of the vibration of said image is given by $$\Delta y = \Delta x \frac{\cos \theta}{\cos \theta'} \sin (\theta' - \theta)$$

where $\Delta y$ is the amplitude of the vibration of the image, $\Delta x$ the amplitude of the vibration of one of the first and second prism means, $\theta$ the angle made by the emerging surface of the first prism means with a plane normal to the optical axis, and $\theta'$ the emerging angle formed when a ray of light incident on the first prism means in parallel with the optical axis emerges therefrom.

5. An apparatus according to claim 2 wherein said prism system means further includes a third prism means provided on the side of the emerging surface of said second prism means, said third prism means having an incident surface and an emerging surface.

6. An apparatus according to claim 5 wherein the emerging surface of said first prism means and the incident surface of said third prism means are positioned opposite to each other and are inclined at the same angle with respect to said optical axis, the incident surface of said second prism means and the emerging surface of said third prism means are positioned opposite to each other and are inclined at the same angle with respect to said optical axis, and said second prism means is vibrated.

7. An apparatus according to claim 1 wherein the emerging surface of said second prism means is inclined relative to the optical axis in such a manner that the normal thereof is located on a plane different from the plane including the normal of the incident surface of said second prism means.

8. An apparatus according to claim 7 wherein the emerging surface of said first prism means is parallel to the incident surface of said second prism means.

9. An apparatus according to claim 8 wherein said prism system means further includes a third prism means provided on the side of the emerging surface of said second prism means in which the emerging surface of said second prism means is parallel to an incident surface of said third prism means.

10. An apparatus according to claim 7 wherein said second prism means comprises a primary prism and a secondary prism into which said second prism means is cut along a plane normal to said optical axis and which are arranged in spaced relation, and said primary and secondary prisms are vibrated along said optical axis.

11. An apparatus according to claim 10 wherein said prism system means further includes a third prism means provided on the side of the emerging surface of said second prism means in which the emerging surface of said first prism and in which an emerging surface of said secondary prism is parallel to an incident surface of said third prism means.

12. An apparatus according to claim 1 wherein said driving means is a piezoelectric device which elongates and contracts in a direction of said optical axis when a power source is turned on.

13. An apparatus according to any one of claims 1, 4, 6 or 8–12 wherein said image receiving means is an incident end face of an optical fiber bundle.

14. An apparatus according to claim 13 wherein said objective lens is arranged in the distal end of a fiber scope and said optical fiber bundle is an image guide fiber bundle provided inside said fiber scope.

15. An apparatus according to claim 13 further comprising an image vibrating means arranged in the vicinity of an emerging end face of said optical fiber bundle and vibrating at the same amplitude and in synchronization with said prism system means for the purpose of cancelling vibration of the image on said emerging end face.

16. An apparatus according to claim 13 further comprising a vibrating means for vibrating an emerging end face of said optical fiber bundle at the same amplitude and in synchronization with said prism system means for the purpose of cancelling vibration of the image on said emerging end face.

17. An apparatus according to claim 13 wherein an image of an object is displayed at an emerging end face of an image guide arranged in a fiber scope and said optical fiber bundle is an image guide provided in a display scope.

18. An apparatus according to any one of claims 1, 4, 6 or 8–12 wherein said image receiving means is a solid-state image sensor.

19. An apparatus according to claim 18 wherein a shutter means is provided between said solid-state image sensor and a surface of said objective lens which is in the closest position to an object and said shutter means brings about a transmission state of light in response to only an area where the amplitude of the vibration of said image incident on said solid-state image sensor becomes maximum.

20. An apparatus according to claim 19 wherein said shutter means is an electro-optic shutter.

21. An apparatus according to claim 19 further including an illuminating means for irradiating light with three kinds of mutually different colors onto the object at a predetermined period in which said solid-state image sensor picks up an image for every transmission state of light of said shutter means and in which said illuminating means and said driving means are set so that one maximum amplitude of said image and another maximum amplitude are included in the period of time during which the light with each of three kinds of mutually different colors is illuminated.

22. An apparatus according to claim 18 wherein said objective lens is arranged in the distal end of a fiber scope and said solid-state image sensor is provided inside said fiber scope.

23. An apparatus according to claim 1 wherein said first and second prism means are so arranged as to be capable of perpendicularly bending an optical path of light having passed through said objective lens.

24. An apparatus according to claim 1 wherein the incident surface of said first prism means and the emerging surface of said second prism means are shaped into curved surfaces.

25. An apparatus according to claim 1 wherein the incident surface of said first prism means is inclined with respect to said optical axis.

* * * * *